(12) United States Patent
Gleichauf et al.

(10) Patent No.: US 6,994,128 B2
(45) Date of Patent: Feb. 7, 2006

(54) STERILE CONTAINER

(75) Inventors: Wilhelm Gleichauf, Tuttlingen-Moehringen (DE); Mariana Jakab, Tuttlingen (DE); Friedrich-Wilhelm Oertmann, Tuttlingen (DE); Torsten Renner, Eisenberg (DE); Stefan Schuster, Tuttlingen (DE); Wolfgang Schwanke, Rietheim-Weilheim (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 10/846,485

(22) Filed: May 13, 2004

(65) Prior Publication Data
US 2004/0256268 A1 Dec. 23, 2004

Related U.S. Application Data

(63) Continuation of application No. PCT/EP02/12671, filed on Nov. 13, 2002.

(30) Foreign Application Priority Data

Nov. 15, 2001 (DE) ............................... 101 56 937
Mar. 6, 2002 (DE) ............................... 102 10 905

(51) Int. Cl.
*B65B 1/04* (2006.01)
(52) U.S. Cl. .................... 141/326; 141/66; 141/325
(58) Field of Classification Search ............... 141/11, 141/63, 64, 66, 69, 325, 326; 422/292–300, 422/26, 28; 220/367.1, 374; 206/439
See application file for complete search history.

(56) References Cited

U.S. PATENT DOCUMENTS

| 4,129,908 A | | 12/1978 | Wagner |
| 4,783,321 A | * | 11/1988 | Spence ...................... 422/300 |
| 4,796,778 A | | 1/1989 | Habig et al. |
| 5,176,884 A | | 1/1993 | Taschner et al. |
| 5,202,098 A | | 4/1993 | Nichols |
| 5,324,489 A | | 6/1994 | Nichols et al. |
| 5,346,075 A | | 9/1994 | Nichols et al. |
| 5,352,416 A | | 10/1994 | Wagner |
| 5,474,738 A | * | 12/1995 | Nichols et al. ............... 422/26 |
| 5,954,219 A | | 9/1999 | Nichols et al. |
| 5,968,459 A | | 10/1999 | Nalepa et al. |
| 6,620,390 B1 | | 9/2003 | Wagner |
| 6,622,871 B2 | | 9/2003 | Gabele et al. |
| 2001/0020601 A1 | | 9/2001 | Gabele et al. |

FOREIGN PATENT DOCUMENTS

| DE | 12 17 551 | 5/1966 |
| DE | 26 10 290 | 9/1976 |
| DE | 34 07 112 | 9/1985 |
| DE | 34 38 463 | 4/1986 |
| DE | 37 11 621 | 10/1987 |
| DE | 37 10 049 | 11/1989 |

(Continued)

*Primary Examiner*—Timothy L. Maust
(74) *Attorney, Agent, or Firm*—Lipsitz & McAllister, LLC

(57) ABSTRACT

The invention relates to a sterile container, especially for receiving and containing surgical instruments or material in sterile conditions, comprising a receiving area formed by a container bottom and container walls, a lid for sealing the receiving are, and a gas exchange opening which can be sealed by a sterile filter maintained in a filter holder. In order to simplify replacement of the sterile filter and to simplify the production of the lid, the sterile filter and filter holder form a filter unit and the filter holder is mounted on the lid.

61 Claims, 3 Drawing Sheets

FOREIGN PATENT DOCUMENTS

| | | |
|---|---|---|
| DE | 41 25 673 | 7/1992 |
| DE | 41 11 077 | 10/1992 |
| DE | 297 20 450 | 2/1998 |
| DE | 197 53 671 | 6/1999 |
| DE | 198 32 823 | 8/1999 |
| WO | 99/27969 | 6/1999 |
| WO | 00/12141 | 3/2000 |

* cited by examiner

STERILE CONTAINER

The present disclosure relates to the subject matter disclosed in international application No. PCT/EP02/12671 of Nov. 13, 2002, which is incorporated herein by reference in its entirety and for all purposes.

BACKGROUND OF THE INVENTION

The invention relates to a sterile container, in particular for the holding and sterile storage of surgical instruments or material, comprising a holding space, which is defined by a container base and container walls, a lid for closing the holding space and a gas exchange opening, which can be closed off by a sterile filter held in a filter holder.

Sterile containers of this type, together with, for example, surgical instruments or material stored therein, are sterilized in a sterilizer. They can then be transferred to a sterile operating region, where they can be opened. The sterile filter is required in order to prevent germs from penetrating into the holding space of the container following the sterilization operation. However, this filter has to be replaced from time to time. In known sterile containers, this can be achieved only with difficulty. Moreover, production of a lid with filter holder arranged integrally thereon is very complex.

Therefore, it is an object of the present invention to improve a sterile container of the type described in the introduction in such a way that the sterile filter can easily be exchanged and the lid is particularly simple to produce.

SUMMARY OF THE INVENTION

In a sterile container of the type described in the introduction, this object is achieved, according to the invention, by virtue of the fact that the sterile filter and the filter holder form a filter unit, and that the filter holder is mounted on the lid.

This configuration allows the filter unit to be exchanged in full if necessary. For this purpose, in particular during insertion, there is no longer any need to take hold of the sterile filter itself, with the result that firstly damage to the filter is avoided, and secondly soiling is prevented. Production of the lid is additionally simplified, since the filter holder can be retrofitted to the lid.

It is advantageous if the sterile filter and the filter holder can be releasably connected, if the sterile filter can be released from the filter holder in a removal position and is held on the filter holder in a connection position. This means that when the filter is being exchanged, only the sterile filter has to be renewed, rather than the entire filter unit. Although the entire filter unit could be exchanged, if the filter holder were still intact it would have been replaced unnecessarily. The overall economic viability of the sterile container is improved as a result.

To prevent damage to the sterile filter, it is advantageous if the sterile filter is held on a carrier element.

To increase the stability and retain the shape of the sterile filter, it is expedient if the carrier element comprises a first and a second support element, and if the sterile filter is held between the two support elements. This allows the sterile filter to be gripped reliably by the carrier element without soiling or damaging the filter.

To further increase the stability of the filter unit, it is possible to provide that at least one of the two support elements comprises supporting sections, which span at least partially the gas exchange opening, for supporting the sterile filter. Although this reduces the size of the gas exchange opening, it also reduces the size of free surfaces of the sterile filter, so that its shape can be stabilized, which is advantageous in particular when pressurized hot steam is applied.

According to a preferred embodiment of the invention, it is possible to provide that the sterile filter, the first and second support elements are nonreleasably connected to one another, in particular by adhesive bonding, clamping or welding. The overall result is a dimensionally stable unit comprising the carrier element and the sterile filter, making it easier to exchange the latter.

The carrier element and the filter holder can be connected to one another in various ways, for example by screw connection or clamping. However, it is particularly advantageous if there is provided a bayonet connection for connecting the carrier element and the filter holder and for transferring the carrier element from the removal position into the connection position. The carrier element can easily be connected to the sterile filter, specifically by the carrier element firstly being inserted into the filter holder and then rotated through a defined angular range, which substantially depends on the number of bayonet projections and recesses which can be brought into engagement with one another and the angular extent thereof. The connection position is usually defined by relative stops between the carrier element and the filter holder, which delimit a rotary movement.

To ensure a defined connection position and to prevent the sterile filter from being released from the filter holder, it is expedient if there is provided a locking mechanism for locking the connection position of the sterile filter and the filter holder.

A locking mechanism can be realized in particularly simple form by a latching connection.

In a further advantageous embodiment of the invention, it is possible to provide that the filter unit comprises a cover for covering the sterile filter on one side. This provides the sterile filter with protection against damage, for example from objects stored in the sterile container, on one side.

To ensure optimum gas exchange and, at the same time, to reliably protect the sterile filter from damage, it may be advantageous if the cover is provided with apertures for allowing gas exchange through the apertures, and if the apertures are covered by aperture covers in a direction which is transverse with respect to a flow-permitting direction.

It is preferable for the cover to be spaced apart from the sterile filter. This prevents the sterile filter from coming into contact with the cover in the event of exposure to hot steam should the sterile filter be deformed, for example bulge out.

Although the cover and the filter holder could be formed integrally, in a preferred embodiment of the invention, however, it is possible to provide that the cover can be releasably connected to the filter holder, that the cover can be detached from the filter holder in a detachment position and is held on the filter holder in a closure position. This allows simple removal of the cover in order to exchange the sterile filter.

The cover could, for example, be secured to the filter holder using screws or clips, but it is particularly advantageous if there is provided a second bayonet connection for connecting the cover and the filter holder and for transferring the cover from the detachment position into the closure position. A connection could, for example, be produced by introducing corresponding projections of the cover into recesses in the filter holder and then rotating the cover as a whole relative to the filter holder. The cover can easily be removed by reversing this operation.

To prevent the cover from unintentionally becoming detached from the filter holder, there is provided a second locking mechanism for locking the cover and the filter holder in the closure position.

The second locking mechanism could, for example, be realized by means of a separately actuable locking element. However, it is particularly simple if the second locking mechanism comprises a second latching connection. This allows all types of latching connections, for example resiliently mounted latching projections, which engage in corresponding recesses.

Furthermore, it is advantageous if the carrier element comprises a centering element, which can be brought into engagement with the cover, in order to center the cover on the filter holder. This in particular facilitates and simplifies fitting of the cover. Moreover, the centering aid can also serve as a stop in order to help to avoid damage to the sterile filter by the cover.

To additionally control and/or regulate gas exchange between the holding space and the vicinity of the sterile container, it may be expedient if the filter unit is mounted moveably, if the filter unit, in a closed position, closes a flow path and, in a flow-permitting position, opens the flow path, so that gas exchange in the closed position is possible only through the sterile filter and in the flow-permitting position is possible through the sterile filter and/or through the flow path. This allows the filter unit, in particular if greater gas exchange is required, to be transferred into the flow-permitting position so that an additional flow path is opened up.

Assembly of the sterile container becomes particularly simple if mounting elements are provided on the filter holder and on the lid for mounting the filter unit on the lid.

A particularly simple structure of the sterile container with a moveably mounted filter unit advantageously results if the mounting elements comprise at least one mounting bolt and an associated mounting bush, if the mounting bolt at each end has a stop for limiting a movement of the mounting bush relative to the mounting bolt, and if the mounting bolt is disposed on the lid and the mounting bush is disposed on the filter holder, or vice versa.

No additional parts are required if one of the two stops is formed by the lid and the other stop is formed by a head of the mounting bolt.

Additional protection for the mounting elements is obtained if the cover covers the mounting elements. In this way, the mounting elements are protected from unintentional manipulation.

To close an additional flow path and thereby to allow objects stored in the sterile container to be kept free of germs, the filter unit is held on the sterile container under preload in the closed position.

A preload of this type can be realized particularly easily if an element which has a preloading action in the longitudinal direction of the mounting bolt is supported between one of the two stops and the mounting bush. Any desired elastic elements, for example coil springs or elastomeric elements, can be used as preloading element.

It is advantageous if there is provided a sealing element for mounting the filter unit on the lid in a gastight manner. This allows complete sealing of the filter unit on the lid, so that gas exchange is possible only through the sterile filter.

It is particularly expedient if the sealing element comprises a sealing ring mounted on the carrier element. Sealing rings are particularly simple to produce and can be disposed on the carrier element in a simple way.

According to a further preferred embodiment of the invention, it is advantageous if there is provided a pressure-relief valve, if the pressure-relief valve is disposed in such a way that in a basic position it adopts a closed position, and if it adopts a flow-permitting position when a pressure in the vicinity of the sterile container exceeds a pressure in the sterile container by a predetermined pressure difference. In this way, it is possible to avoid damage to the sterile container, since the pressure-relief valve opens, allowing gas to flow into the container, before the sterile container can be deformed as a result of a particularly high pressure in the surrounding region or a correspondingly high pressure gradient.

No additional components or further apertures are required if the filter unit forms the pressure-relief valve. The filter unit therefore performs two functions; firstly it serves to block germs, and secondly it serves as a pressure-relief valve.

There is preferably provided a protective element which covers the filter unit at a spacing therefrom. This in particular makes it possible to reliably protect the sterile filter against mechanical damage.

It is particularly expedient if the filter unit is mounted on an inner side of the lid and if the protective element is disposed on an outer side of the lid. This means that the filter unit comprising the sterile filter is reliably protected against mechanical damage from both sides.

To minimize the amount of liquid which reaches the sterile filter, it is advantageous if between the protective element and the lid there is provided at least one opening for the passage of gas, which is in fluid communication with the gas exchange opening and is disposed in such a way that gas flow is possible in a direction of flow running substantially transversely with respect to the flow-permitting direction of the sterile filter. In this way, gas, for example hot steam for sterilization, can easily pass through the sterile filter, whereas liquids are initially kept away from the sterile filter.

To make it even more difficult for liquids to penetrate into the filter unit, it is expedient if there is provided an inflow edge which is disposed on the outer side of the lid, faces away from the gas exchange opening and slopes downward toward the outside relative to a lid plane. If liquid reaches the lid, the inclination of the inflow edge away from the gas exchange opening means that it can flow away and therefore cannot reach the filter unit.

To facilitate installation of the filter holder and to increase the stability of the latter, in a preferred embodiment of the invention it is provided that the filter holder is mounted on the lid in a manner which is secured against rotation.

It is preferable for the sterile filter to be a long-term filter, in particular made from polytetrafluoroethylene (PTFE). This makes it possible to extend the intervals between maintenance of the sterile container, meaning that the filter unit only seldom has to be exchanged.

The sterile container becomes particularly efficient and simple to produce if the lid is made from a plastic, in particular from polyether ether ketone (PEEK) or polyphenylene sulfone (PPSU).

BRIEF DESCRIPTION OF THE DRAWINGS

The following description of a preferred embodiment of the invention, in conjunction with the drawing, serves to provide a more detailed explanation. In the drawing.

DETAILED DESCRIPTION OF THE INVENTION

Figure 1:
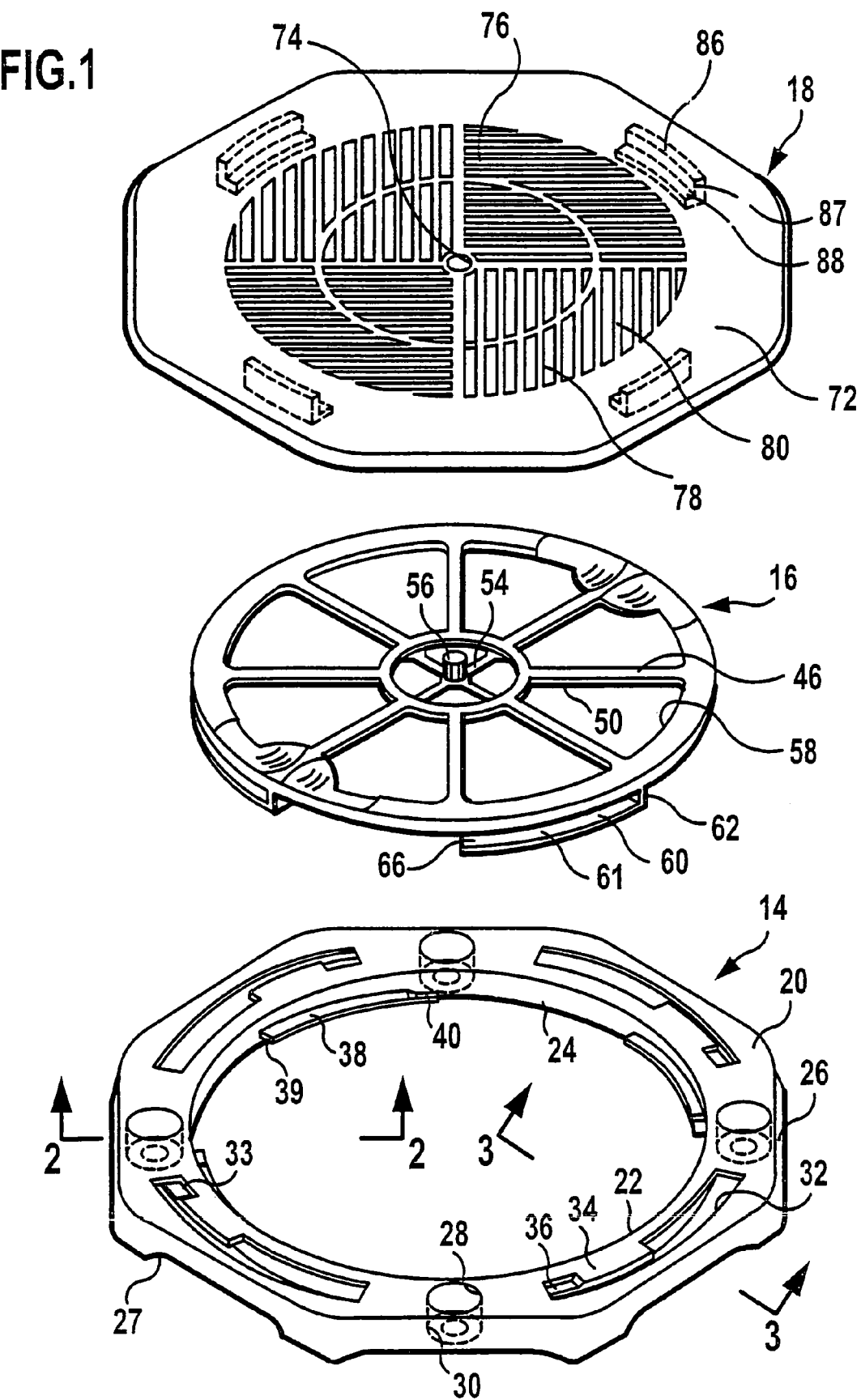
FIG. 1: shows an exploded view of a dismantled, three-part filter unit.
Figure 2:
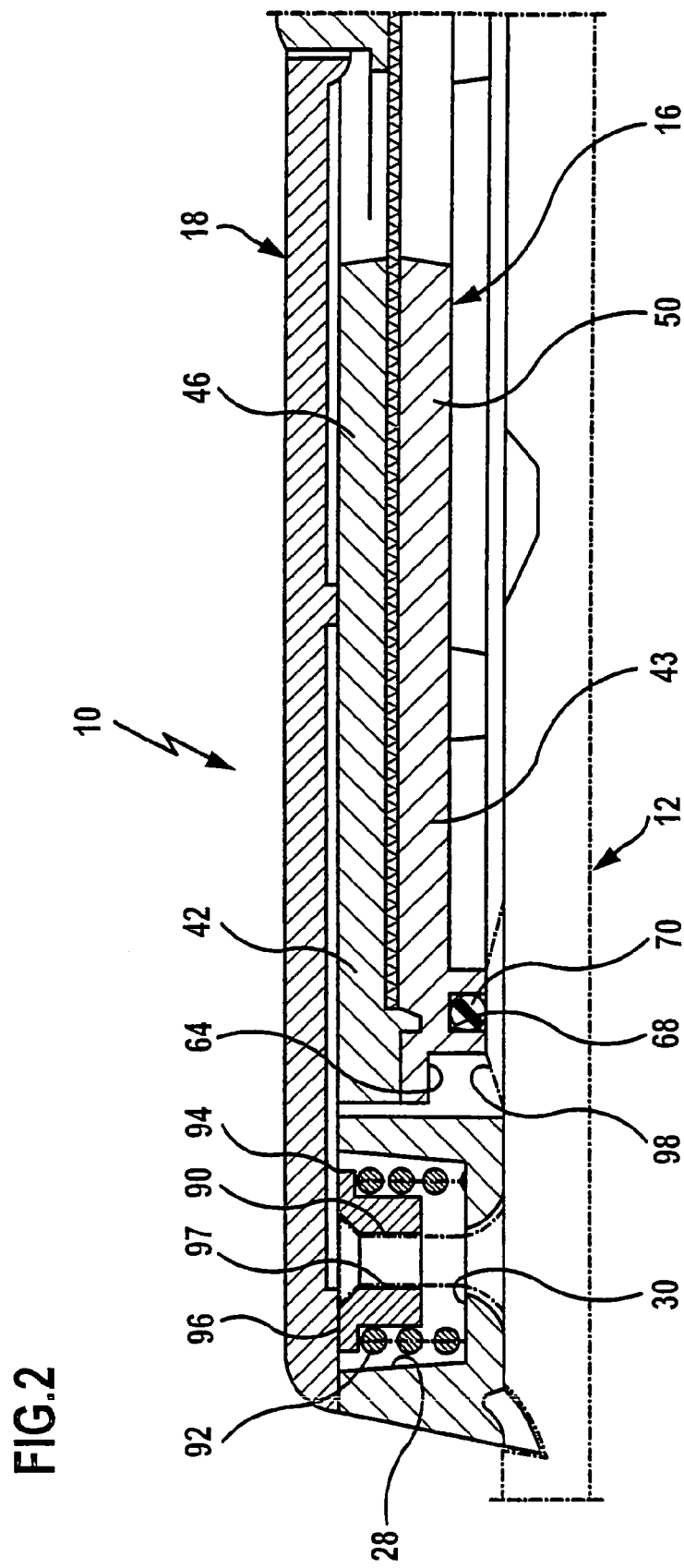
FIG. 2: shows a sectional view on line 2—2 in FIG. 1.
Figure 3:
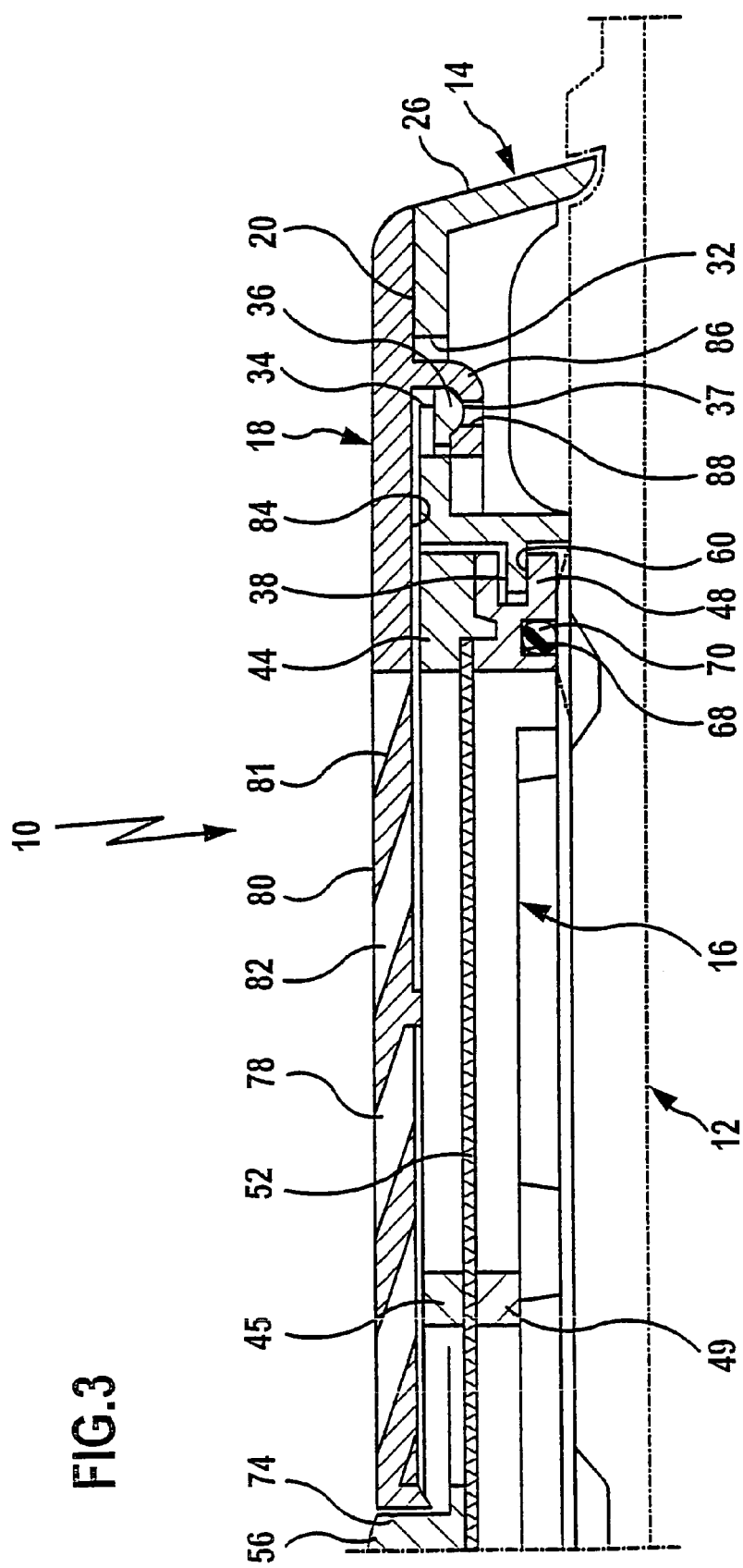
FIG. 3: shows a sectional view on line 3—3 in FIG. 1.

FIGS. 1 to 3 illustrate a three-part filter unit, which is denoted overall by reference numeral 10 and is mounted on a lid 12 of a sterile container (not shown in more detail).

The filter unit 10 comprises a holding frame 14, which can be connected to the lid 12, a filter element 16, which can be placed into the holding frame 14 and connected to the latter, and a cover 18 which can be connected to the holding frame 14.

The holding frame 14 comprises a cover plate 20 which has an octagonal external contour and also has a circular opening 22 surrounded by an encircling inner rim 24. An encircling outer rim 26 adjoins the octagonal outer contour of the cover plate 20, so that a hollow profile which is substantially U-shaped in cross section is formed. Four identical cylindrical sleeves, serving as mounting bushes 28, are inserted into the cover plate, in each case offset by 90° in the circumferential direction, which sleeves, at their end remote from the cover plate 20, have an annular flange 30 facing inward and running parallel to the cover plate 20. Between the mounting bushes 28 are disposed four identical slots 32, which extend over an angular range of approximately 45° and are partially covered by a projection 34, which is formed integrally with the cover plate 20 and is adjoined by an integrally formed, resilient latching lug 36 which faces in the circumferential direction, which can be moved to a slight extent perpendicular to the cover plate 20 and, on a side facing away from the cover plate 20, has a small spherical projection (not shown). The projection 34 and the latching lug 36 cover approximately 40% of the slot 32 in the circumferential direction starting from one end of the slot 32.

Furthermore, the inner rim 24 is provided with four radial projections 38, which are distributed symmetrically over the circumference, extend in the circumferential direction, project radially inward and extend over an angular range of approximately 40°. On one side, the radial projections 38 are extended by latching tongues 40 which protrude in a parallel offset manner and can be moved to a slight extent perpendicular to the cover plate 20.

A free rim contour 27, facing away from the cover plate 20, of the outer rim 26 is partially curved and configured so as to correspond to an inner surface (not shown in more detail) of the lid 12, so that it is possible to realize positively locking placement of the holding frame 14 against the lid 12.

The filter element 16 comprises two clamping disks 42 and 43, which have an inner ring 45 and 49, respectively, in each case connected via eight radially extending webs 46 and 50, respectively, to an outer ring 44 and 48, respectively. Four holding webs 54, which are disposed in a cross shape and centrally carry a centering projection 56, pass through the inner ring 45 of the clamping disk 42. Between the clamping disks 42 and 43 there is a sterile filter 52 which completely covers the annular opening 58 delimited by the outer rings 44 and 48. The two clamping disks 42 and 43 and the sterile filter 52 are fixedly connected to one another, for example by adhesive bonding or ultrasound welding, and form a single unit.

The external diameter of the annular filter element 16 corresponds to the internal diameter of the opening 22 of the holding frame 14 and can therefore be inserted into this opening 22. To connect the filter element 16 to the holding frame 14, the outer ring 48 is provided with four receiving grooves 60, which are distributed symmetrically over the circumference and are open to the radially outer side. In each case one lateral end of the receiving groove 60 is closed off by a groove end wall 62. The filter element 16 is inserted into the holding frame 14 in such a manner that the four receiving grooves 60 engage between those regions of the inner rim 24 which are provided with the radial projections 38. A radially protruding outer annular flange 64 of the outer ring 48 in this position is supported on the radial projections 38. The filter element 16 is then rotated until the groove end wall 62 comes to a stop against the end edge 39 of the radial projection 38 engaging in the receiving groove 60. In this connection position of the holding frame 14 and the filter element 16, the projections disposed on the latching tongue 40 penetrate into corresponding recesses 66 at the open end of in each case one side wall 61 of the receiving groove, resulting in latching locking of the connection position.

Furthermore, the outer ring 48 is provided with an annular groove 68 which is open in the direction facing away from the outer ring 44 and into which a sealing ring 70 is inserted.

The filter unit 10 is closed off by means of the cover 18, which has an octagonal baseplate 72 which corresponds to the outer contour of the cover plate 20 and is provided with a central bore 74 for introduction of the centering projection 56. A circular surface region 76 is provided with slots 78 of different lengths in each case running parallel in quarter-circle sectors, so that webs 80 remain between the slots 78, protruding as extensions running obliquely, approximately at an angle of 60°, relative to the baseplate 72. Obliquely running web regions form aperture covers 81 that in each case completely cover the slots 78, so that obliquely extending passages 82 are formed in each case. Direct passage through the slots 78 perpendicular to the baseplate 72 is not possible.

Four symmetrically distributed retaining projections 86, which are L-shaped in cross section, extend over an angular range of approximately 30° and one free limb of which, at one of its ends, has a bore 88 running perpendicular to the baseplate 72, project from an underside 84 of the baseplate 72.

The cover 18 is connected to the holding frame 14 in the following way: the cover 18 is introduced, by means of the retaining projections 86, into regions of the slots 32 which are not covered by projections 34, until the underside 84 of the baseplate 72 bears against the cover plate 20. Rotation of the cover 18 in the clockwise direction causes the free limbs of the retaining projections 86 to engage behind the projections 34 until an end side 87 of the retaining projection 86 comes to a stop at an end edge 33 of the slot 32. In this closure position, a hemisphere 37 disposed on the latching lug 36 penetrates into the bore 88 and locks the closure position of the cover 18 and of the holding frame 14.

The securing of the holding frame 14 to the lid 12 is explained in conjunction with FIG. 2. On the lid 12, adjacent to a circular aperture (not shown), on its inner side there are disposed four substantially cylindrical holding bolts 90 protruding perpendicularly away from the lid 12. The mounting bushes 28 of the holding frame 14 are pushed over the holding bolts 90, so that the annular flanges 30 engage against the inner side of the lid 12, surrounding the holding bolts 90. Each holding bolt 90 is surrounded by a coil spring 92, which on one side is supported against the annular flange 30 and on the other side is supported against an annular flange 94 of a cover 96 which has a central bore 97, the internal diameter of which corresponds to the external diameter of the holding bolt 90. The cover 96 is ultrasonically welded or adhesively bonded to the holding bolt.

This mounting arrangement makes it possible for the entire filter unit 10 to be lifted off the inner side of the lid 12 counter to the prestress of the coil springs 92. This occurs, for example, if a sterile container with a filter unit 10 disposed thereon is introduced into a sterilizer and acted on by pressurized hot steam. The pressure surrounding the sterile container is in this case higher than the pressure in the interior of the container, so that the entire filter unit 10 lifts off the lid 12 and opens up an additional flow path for hot steam to flow in. This prevents the sterile container from being deformed by the action of excessive pressure differences. If the externally acting pressure drops again, the filter unit 10 is preloaded onto the inner side of the lid 12 by means of the coil springs 92. The sealing ring 70, in this closed position, engages against a corresponding sealing projection 98 of the lid 12, so that gas exchange is then only possible through the sterile filter 52 into the interior of the sterile container. On account of this resilient mounting, the entire filter unit 10 simultaneously also performs the function of a pressure-relief valve.

What is claimed is:

1. Sterile container, in particular for the holding and sterile storage of surgical instruments or material, comprising:
    a holding space defined by a container base and container walls,
    a lid for closing the holding spaces,
    a filter holder mounted on said lid,
    a sterile filter held in said filter holder, the sterile filter and the filter holder forming a filter unit, and
    a gas exchange opening being closeable by said sterile filter,
    wherein:
    the filter unit, in a closed position, closes a flow path and, in a flow-permitting position, opens the flow path, so that gas exchange in the closed position is possible only through the sterile filter and in the flow-permitting position is possible through the sterile filter and/or through the flow path.

2. Sterile container according to claim 1, wherein the sterile filter and the filter holder can be releasably connected, in that the sterile filter can be released from the filter holder in a removal position and is held on the filter holder in a connection position.

3. Sterile container according to claim 1, wherein the sterile filter is held on a carrier element.

4. Sterile container according to claim 3, wherein the carrier element comprises a first and a second support element, and wherein the sterile filter is held between the two support elements.

5. Sterile container according to claim 4, wherein at least one of the two support elements comprises supporting sections, which span at least partially the gas exchange opening, for supporting the sterile filter.

6. Sterile container according to claim 4, wherein the sterile filter, the first and second support elements are nonreleasably connected to one another, in particular by adhesive bonding, clamping or welding.

7. Sterile container according to claim 2, wherein there is provided a bayonet connection for connecting the carrier element and the filter holder and for transferring the carrier element from the removal position into the connection position.

8. Sterile container according to claim 2, wherein there is provided a locking mechanism for locking the connection position of the sterile filter and the filter holder.

9. Sterile container according to claim 8, wherein the locking mechanism comprises a latching connection.

10. Sterile container according to claim 1, wherein the filter unit comprises a cover for covering the sterile filter on one side.

11. Sterile container according to claim 3, wherein the filter unit comprises a cover for covering the sterile filter on one side.

12. Sterile container according claim 10, wherein the cover is provided with apertures for allowing gas exchange through the apertures, and wherein the apertures are covered by aperture covers in a direction which is transverse with respect to a flow-permitting direction.

13. Sterile container according to claim 10, wherein the cover is spaced apart from the sterile filter.

14. Sterile container according to claim 10, wherein the cover can be releasably connected to the filter holder, and wherein the cover can be detached from the filter holder in a detachment position and is held on the filter holder in a closure position.

15. Sterile container according to claim 14, wherein there is provided a second bayonet connection for connecting the cover and the filter holder and for transferring the cover from the detachment position into the closure position.

16. Sterile container according to claim 14 wherein there is provided a second locking mechanism for locking the cover and the filter holder in the closure position.

17. Sterile container according to claim 16, wherein the second locking mechanism comprises a second latching connection.

18. Sterile container according to claim 10, wherein the carrier element comprises a centering element, which can be brought into engagement with the cover, in order to center the cover on the filter holder.

19. Sterile container according to claim 1, wherein mounting elements are provided on the filter holder and on the lid for mounting the filter unit on the lid.

20. Sterile container according to claim 3, wherein mounting elements are provided on the filter holder and on the lid for mounting the filter unit on the lid.

21. Sterile container according to claim 10, wherein mounting elements are provided on the filter holder and on the lid for mounting the filter unit on the lid.

22. Sterile container according to claim 19, wherein the mounting elements comprise at least one mounting bolt and an associated mounting bush, wherein the mounting bolt at each end has a stop for limiting a movement of the mounting bush relative to the mounting bolt, and wherein the mounting bolt is disposed on the lid and the mounting bush is disposed on the filter holder, or vice versa.

23. Sterile container according to claim 22, wherein one of the two stops is formed by the lid and the other stop is formed by a head of the mounting bolt.

24. Sterile container according to claim 19, wherein:
    the filter unit comprises a cover for covering the sterile filter on one side, and
    the cover covers the mounting elements.

25. Sterile container according to claim 1, wherein the filter unit is held on the sterile container under preload in the closed position.

26. Sterile container according to claim 25, wherein an element which has a preloading action in the longitudinal direction of the mounting bolt is supported between one of the two stops and the mounting bush.

27. Sterile container according to claim 1, wherein there is provided a sealing element for mounting the filter unit on the lid in a gastight manner.

28. Sterile container according to claim 3, wherein there is provided a sealing element for mounting the filter unit on the lid in a gastight manner.

29. Sterile container according to claim 10, wherein there is provided a sealing element for mounting the filter unit on the lid in a gastight manner.

30. Sterile container according to claim 19, wherein there is provided a sealing element for mounting the filter unit on the lid in a gastight manner.

31. Sterile container according to claim 27, wherein the sealing element comprises a sealing ring mounted on the carrier element.

32. Sterile container according to claim 1, wherein there is provided a pressure-relief valve, wherein the pressure-relief valve is disposed in such a way that in a basic position it adopts a closed position, and wherein it adopts a flow-permitting position when a pressure in the vicinity of the sterile container exceeds a pressure in the sterile container by a predetermined pressure difference.

33. Sterile container according to claim 3, wherein there is provided a pressure-relief valve, wherein the pressure-relief valve is disposed in such a way that in a basic position it adopts a closed position, and wherein it adopts a flow-permitting position when a pressure in the vicinity of the sterile container exceeds a pressure in the sterile container by a predetermined pressure difference.

34. Sterile container according to claim 10, wherein there is provided a pressure-relief valve, wherein the pressure-relief valve is disposed in such a way that in a basic position it adopts a closed position, and wherein it adopts a flow-permitting position when a pressure in the vicinity of the sterile container exceeds a pressure in the sterile container by a predetermined pressure difference.

35. Sterile container according to claim 32, wherein the filter unit forms the pressure-relief valve.

36. Sterile container according to claim 1, wherein there is provided a protective element which covers the filter unit at a spacing therefrom.

37. Sterile container according to claim 3, wherein there is provided a protective element which covers the filter unit at a spacing therefrom.

38. Sterile container according to claim 10, wherein there is provided a protective element which covers the filter unit at a spacing therefrom.

39. Sterile container according to claim 36, wherein the filter unit is mounted on an inner side of the lid, and wherein the protective element is disposed on an outer side of the lid.

40. Sterile container according to claim 36, wherein between the protective element and the lid there is provided at least one opening for the passage of gas, which is in fluid communication with the gas exchange opening and is disposed in such a way that gas flow is possible in a direction of flow running substantially transversely with respect to the flow-permitting direction of the sterile filter.

41. Sterile container according to claim 1, wherein there is provided an inflow edge which is disposed on the outer side of the lid, faces away from the gas exchange opening and slopes downward toward the outside relative to a lid plane.

42. Sterile container according to claim 10, wherein there is provided an inflow edge which is disposed on the outer side of the lid, faces away from the gas exchange opening and slopes downward toward the outside relative to a lid plane.

43. Sterile container according to claim 19, wherein there is provided an inflow edge which is disposed on the outer side of the lid, faces away from the gas exchange opening and slopes downward toward the outside relative to a lid plane.

44. Device according to claim 1, wherein the filter holder is mounted on the lid in a manner which is secured against rotation.

45. Sterile container according to claim 1, wherein the sterile filter is a long-term filter, in particular made from polytetrafluoroethylene (PTFE).

46. Sterile container according to claim 1, wherein the lid (12) is made from a plastic, in particular from polyether ether ketone (PEEK) or polyphenylene sulfone (PPSU).

47. Sterile container, in particular for the holding and sterile storage of surgical instruments or material, comprising:
a holding space defined by a container base and container walls,
a lid for closing the holding space,
a filter holder mounted on said lid,
a sterile filter held in said filter holder, the sterile filter and the filter holder forming a filter unit,
a gas exchange opening being closeable by said sterile filter, and
mounting elements provided on the filter holder and on the lid for mounting the filter unit on the lid, said mounting elements comprising at least one mounting bolt and an associated mounting bush, said mounting bolt at each end having a stop for limiting a movement of the mounting bush relative to the mounting bolt, said mounting bolt being disposed on the lid and the mounting bush being disposed on the filter holder, or vice versa.

48. Sterile container according to claim 47, wherein one of the two stops is formed by the lid and the other stop is formed by a head of the mounting bolt.

49. Sterile container according to claim 47, wherein there is provided an inflow edge which is disposed on the outer side of the lid, faces away from the gas exchange opening and slopes downward toward the outside relative to a lid plane.

50. Sterile container, in particular for the holding and sterile storage of surgical instruments or material, comprising:
a holding space defined by a container base and container walls,
a lid for closing the holding space,
a filter holder mounted on said lid,
a sterile filter held in said filter holder, the sterile filter and the filter holder forming a filter unit,
a gas exchange opening being closeable by said sterile filter, and
mounting elements provided on the filter holder and on the lid for mounting the filter unit on the lid,
said filter unit comprising a cover for covering the sterile filter on one side, wherein the cover covers the mounting elements.

51. Sterile container according to claim 50, wherein there is provided an inflow edge which is disposed on the outer side of the lid, faces away from the gas exchange opening and slopes downward toward the outside relative to a lid plane.

52. Sterile container, in particular for the holding and sterile storage of surgical instruments or material, comprising:
a holding space defined by a container base and container walls,
a lid for closing the holding space, a filter holder mounted on said lid, a sterile filter held in said filter holder, the sterile filter and the filter holder forming a filter unit, a gas exchange opening being closeable by said sterile filter, and a pressure-relief valve, said pressure-relief valve being disposed in such a way that in a basic position it adopts a closed position, and that it adopts a flow-permitting position when a pressure in the vicinity of the sterile container exceeds a pressure in the sterile container by a predetermined pressure difference.

53. Sterile container according to claim 52, wherein the sterile filter is held on a carrier element.

54. Sterile container according to claim 52, wherein the filter unit comprises a cover for covering the sterile filter on one side.

55. Sterile container, in particular for the holding and sterile storage of surgical instruments or material, comprising:

a holding space defined by a container base and container walls, a lid for closing the holding space, a filter holder mounted on said lid, a sterile filter held in said filter holder, the sterile filter and the filter holder forming a filter unit, a gas exchange opening being closeable by said sterile filter, and a protective element which covers the filter unit at a spacing therefrom, said filter unit being mounted on an inner side of the lid, and said protective element being disposed on an outer side of the lid.

56. Sterile container according to claim 55, wherein the sterile filter is held on a carrier element.

57. Sterile container according to claim 55, wherein the filter unit comprises a cover for covering the sterile filter on one side.

58. Sterile container according to claim 55, further comprising at least one opening for the passage of gas which is provided between the protective element and the lid, said at least one opening for the passage of gas being in fluid communication with the gas exchange opening and being disposed in such a way that gas flow is possible in a direction of flow running substantially transversely with respect to the flow-permitting direction of the sterile filter.

59. Sterile container, in particular for the holding and sterile storage of surgical instruments or material, comprising:

a holding space defined by a container base and container walls, a lid for closing the holding space, a filter holder mounted on said lid, a sterile filter held in said filter holder, the sterile filter and the filter holder forming a filter unit, a gas exchange opening being closeable by said sterile filter, and an inflow edge being disposed on the outer side of the lid, facing away from the gas exchange opening and sloping downward toward the outside relative to a lid plane.

60. Sterile container according to claim 59, wherein the filter unit comprises a cover for covering the sterile filter on one side.

61. Sterile container according to claim 59, wherein mounting elements are provided on the filter holder and on the lid for mounting the filter unit on the lid.

* * * * *

UNITED STATES PATENT AND TRADEMARK OFFICE
CERTIFICATE OF CORRECTION

| | |
|---|---|
| PATENT NO. | : 6,994,128 B2 |
| APPLICATION NO. | : 10/846485 |
| DATED | : February 7, 2006 |
| INVENTOR(S) | : Gleichauf et al. |

It is certified that error appears in the above-identified patent and that said Letters Patent is hereby corrected as shown below:

Column 7, line 25: Delete the "s" at the end of the word "spaces".

Signed and Sealed this

Eighth Day of August, 2006

JON W. DUDAS
*Director of the United States Patent and Trademark Office*